US00PP10750P

United States Patent [19]

Meserve

[11] Patent Number: Plant 10,750

[45] Date of Patent: Jan. 12, 1999

[54] ILEX PLANT NAMED 'CENTENNIAL GIRL'

[75] Inventor: Kathleen K. Meserve, Vero Beach, Fla.

[73] Assignee: The Conard-Pyle Company, West Grove, Pa.

[21] Appl. No.: 885,364

[22] Filed: Jun. 30, 1997

[51] Int. Cl.[6] ..... A01H 5/00

[52] U.S. Cl. ..... Plt./65

[58] Field of Search ..... Plt./65

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

A new and distinct Ilex variety is provided which originated by the crossing of an unnamed and unpatented plant of *Ilex centrochinensis* with an unnamed and unpatented plan of *Ilex aquifolium*. The resulting evergreen shrub or tree is densely-formed, naturally pyramidal, and forms a vigorous head branch. The leaves are a dark green with a satin finish and possess spines that lack a propensity to catch clothing. The boldly colored berries are bright red, extremely long lasting, and are borne in clusters in profusion. The cold tolerance and tolerance to diseases, such as Tar Spot and Anthracnose, is good.

1 Drawing Sheet

SUMMARY OF THE INVENTION

The present invention relates to a new and distinct female cultivar of Ilex which originated during the course of a planned breeding program carried out by me at St. James, Long Island, N.Y. The female parent (i.e., seed parent) was an unnamed and unpatented plant of *Ilex centrochinensis* and the male parent (i.e., pollen parent) was an unnamed and unpatented plant of *Ilex aquifolium*, (i.e., English Holly). The objective of the breeding and selection procedure was to form and discover a new cultivar having excellent hardiness, an attractive upright growth habit, a propensity of forming attractive fruit in abundance, and adaptability to fulfill a wide variety of landscape needs. The parent of the new variety can be summarized as follows:

*Ilex centrochinesis×Ilex aquifolium.*

From among the offspring of the cross a single plant of the new cultivar of the present invention was selected and preserved since it was found to well meet the objectives of the breeding program. It was found that the new and distinct female *Ilex centrochinensis×aquifolium* cultivar of the present invention:

(a) assumes the configuration of a densely-formed naturally pyramidal evergreen shrub or small tree having a vigorous head branch,
(b) forms attractive dark green leaves having a satin finish and spines that generally lack a propensity to catch clothing,
(c) forms in clusters in profusion berries that are bright red in coloration and long lasting on the plant when mature, and
(d) exibits cold tolerance that exceeds that of *Ilex aquifolium.*

The new cultivar inherently assumes a pyramidal configuration in the absence of pruning, and well retains its shape following pruning. The red berries are highly visible and provide a nicely contrasting coloration to the landscape. Such berries also are extremely long lasting on the plant and commonly are retained on the plant well in March. The cold tolerance of the new cultivar generally makes possible growing into U.S.D.A. Plant-Hardiness Zone 5. For instance, the new variety when grown in the unprotected landscape has survived temperatures of approximately −30°C. when tested at Northern Ohio. Such hardiness of the new cultivar accordingly exceeds that of the *Ilex aquifolium* parent. The disease tolerance of the new cultivar additionally has been good. The new Ilex cultivar of the present invention can be grown to advantage in the landscape as a distinctive specimen plant or combined with other plants to form a unique privacy screen, etc. The boldly colored berries add vivid coloration to the winter landscape. Asexual propagation of the new cultivar by cuttings has been carried out at St. James, Long Island, N.Y., and at West Grove, Pa. Such propagation has confirmed that the unique combination of characteristics of the new cultivar has been stably established and is well transmitted to successive generations. The new cultivar of the present invention has been named 'Centennial Girl'.

BRIEF DESCRIPTION OF THE PHOTOGRAPHS

The accompanying photographs show as nearly true as it is reasonably possible to make the same, in a color illustration of this character, typical specimens of the new cultivar. The plants illustrated were photographed during February 1996 while growing in the open landscape at West Grove, Pa. FIG. 1 illustrates a mature plant of the 'Centennial Girl' cultivar having a height of approximately 4 to 5 meters and a width of approximately 2 to 3 meters. The dense naturally pyramidal growth habit is illustrated as well as the attractive dark green foliage and profusion of red berries. Such plant had undergone little or no pruning. FIG. 2 illustrates a close-up view of representative foliage and berries of the plant of FIG. 1. The satin and spines of the foliage are visible. The attractive berries are shown to be borne in numerous adjacent clusters.

DETAILED DESCRIPTION

Figure 1:
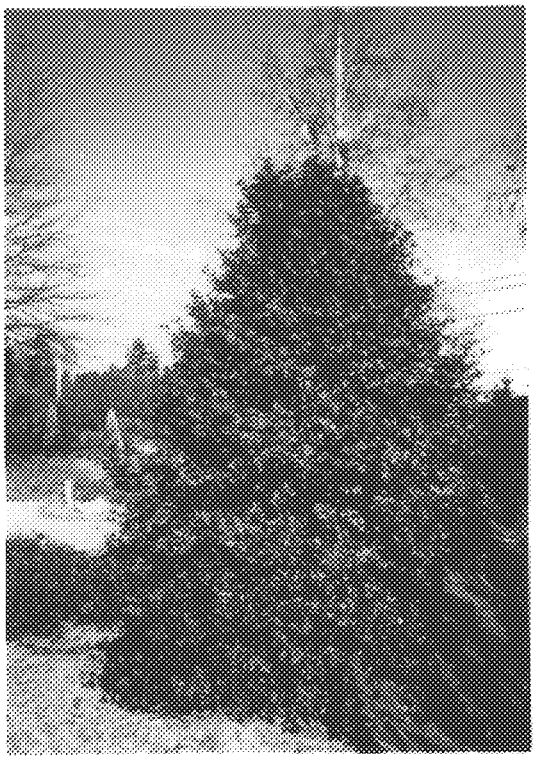
Figure 2:
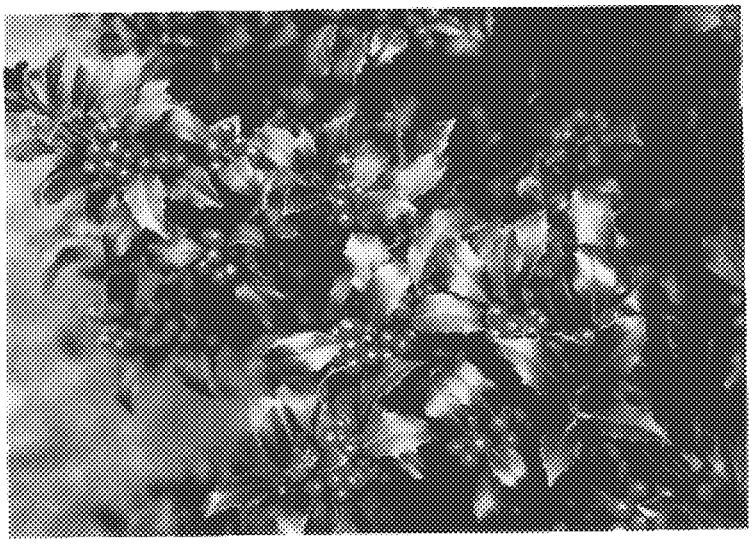

The following is a detailed description of the new cultivar of the present invention which was prepared while observing fifteen year-old plants growing in the ground at West Grove, Pa. Color terminology is in accordance with the R.H.S. Colour Chart of The Royal Horticultural Society, London, England, except where general color terms of ordinary dictionary significance are used.

Type: Hardy broad-leaved shryb or small tree for garden decoration or general landscape use.

Parentage: *Ilex centrochinensis*×*Ilex aquifolium.*

Propagation: It holds its distinguishing characteristics through succeeding propagations by vegetative or asexual propagation methods, such as the rooting of vegetative cuttings.

Foliage:

*Type.*—Evergreen. Leaves are ovate — oblong elliptic with an acute acuminate apex and a cuneate base. The shape and size of the spines is substantially constant throughout the plant. Number of spines varies commonly from 9 to 14 per leaf. There commonly are 6 to 7 spines on each side of a leaf. The leaf margins are sinuate spinose undulate. The leaf tips are refous. The new foliage tends to be somewhat more pointed than the mature foliage. The leaves possess a satin appearance (as illustrated) on both surfaces. During the winter, the under surface may tend to assume a matte appearance and to become less glossy.

*Size.*—Mature leaves on a main stem when measuring to the tips of the spines commonly are approximately 4 to 6 cm. in length on average, and approximately 2 to 2.5 cm. in width on average. The new foliage tends to be smaller in size than the mature foliage. Also, the mature foliage tends to be more leathery than the immature foliage.

*Petiole.*—Commonly approximately 1/10 of the length of the foliage on average. The upper surface is Yellow-Green Group 146B and the lower side is Yellow-Green Group 144B.

*Color.*—When observed during May, mature leaves are on the upper surface commonly are between Yellow-Green Group 147A and Green group 139A, and on the under surface are near Yellow-Green Group 146A; and juvenile leaves are Yellow-Green Group 144A with highlights of Greyed-Orange Group 176A, and on the under surface are Yellow-Green Group 144A with highlights of Greyed-Orange Group 176A with a midrib of Yellow-Green Group 144C. When observed during February, mature leaves are on the upper surface are Yellow-green Group 147A with black overtones, and on the under surface are Yellow-Green Group 146A; and juvenile leaves are Yellow-Green Group 147A, and on the under surface are Yellow-Green Group 146A. Young stems are Brown Group 200A with an overtone of Grey Group 201A, and mature stems are Brown Group 200A mottled with Grey-Brown Group 199B and Green Group 143A.

*Stems.*—Commonly possess a diameter of approximately 4 mm. on juvenile foliage and approximately 8 mm. on adult foliage.

Inflorescence:

*Bud.*—Color: Near Green-White Group 157B.

*Bloom.*—Color: White Group 155A on the upper surface and Green-White Group 157B on the lower surface.

*Berries.*—The berries are substantially round, very abundant, approximately 6 to 8 mm. in diameter, and globose to sub-globose. The stigma is four-lobed explanate quadrangular. The pedicels are approximately 5 to 6 mm. in length, and rufous with two sub-basal ciliate prophylla. The calyx is explanate, quadrangular in outline. The mature color of the berries is near Red Group 45A. The berries commonly are borne in multiple clusters of up to six berries.

Development:

*Hardiness.*—The hardiness has been observed to exceed that of the *Ilex aquifolium* (i.e., English Holly) parent.

*Disease tolerance.*—Good tolerance to Tap Spot and Anthracnose has been observed.

*Insect tolerance.*—Damage caused by Holly Leaf Miner has not been a problem.

I claim:

1. A new and distinct female *Ilex centrochinensis*×*Ilex aquifolium* plant possessing the following characteristics:

(a) assumes the configuration of a densely-formed naturally pyramidal evergreen shrub or small tree having a vigorous head branch, (b) forms attractive dark green leaves having a satin finish and spines that generally lack a propensity to catch clothing, (c) forms in clusters in profusion berries that are bright red in coloration and long lasting on the plant when mature, and (d) exhibits cold tolerance that exceeds that of *Ilex aquifolium:* substantially as illustrated and described.

* * * * *